United States Patent
Hands et al.

(10) Patent No.: US 10,485,892 B2
(45) Date of Patent: Nov. 26, 2019

(54) METHOD FOR LOCAL REDUCTION OF MICROBIAL SKIN FLORA

(71) Applicant: Covalon Technologies Inc., Mississauga (CA)

(72) Inventors: John Richard Hands, Richmond Hill (CA); Valerio Ditizio, Toronto (CA)

(73) Assignee: Covalon Technologies Inc., Mississauga (CA)

( * ) Notice: Subject to any disclaimer, the term of this patent is extended or adjusted under 35 U.S.C. 154(b) by 0 days.

(21) Appl. No.: 15/065,610

(22) Filed: Mar. 9, 2016

(65) Prior Publication Data

US 2016/0263270 A1 Sep. 15, 2016

Related U.S. Application Data

(60) Provisional application No. 62/130,921, filed on Mar. 10, 2015.

(51) Int. Cl.
| | |
|---|---|
| *A61L 15/26* | (2006.01) |
| *A61L 15/44* | (2006.01) |
| *A61L 15/58* | (2006.01) |
| *A61L 26/00* | (2006.01) |
| *A61L 15/46* | (2006.01) |

(52) U.S. Cl.
CPC .............. *A61L 15/58* (2013.01); *A61L 15/46* (2013.01); *A61L 2300/104* (2013.01); *A61L 2300/206* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 8,778,387 B2 | 7/2014 | Tennican et al. | |
| 2009/0104252 A1 | 4/2009 | Alam et al. | |
| 2011/0290259 A1 | 12/2011 | McGuire, Jr. et al. | |
| 2012/0330210 A1* | 12/2012 | Yang | A61K 31/155 602/48 |
| 2013/0189339 A1 | 7/2013 | Vachon | |
| 2013/0204212 A1 | 8/2013 | Tennican | |

FOREIGN PATENT DOCUMENTS

| | | |
|---|---|---|
| CA | 2883373 | 3/2014 |
| WO | 2007010296 | 1/2007 |
| WO | 2011156910 | 12/2011 |

OTHER PUBLICATIONS

International Search Report and Written Opinion dated Nov. 12, 2015 in relation to PCT Application No. PCT/CA2015/050181, filed on Mar. 10, 2015.
Sawada Y., et al. "Silicone gel including antimicrobial agent", Brit. J. Plast. Surg., 1990, 43(1): 78-82.
Sawada Y., et al. "A silicone gel sheet dressing containing an antimicrobial agent for split thickness donor site wounds", Brit. J. Plast. Surg., 1990, 43(1): 88-93.

* cited by examiner

*Primary Examiner* — Bethany P Barham
*Assistant Examiner* — Peter Anthopolos

(57) ABSTRACT

There is provided a method for reducing microbial load at a site on the skin of a subject. The method comprises applying a dressing over the site on the skin of the subject at which a medical procedure that involves breaching the skin is to be performed. As used in the method, the dressing comprises a self-adhesive silicone gel sheet comprising at least about 95 wt % silicone and up to about 5 wt % of particulates of an antimicrobial dispersed in the silicone. The dressing is applied with the silicone gel sheet contacting the skin of the subject and is left in place to allow the antimicrobial to diffuse onto the site.

17 Claims, 1 Drawing Sheet

METHOD FOR LOCAL REDUCTION OF MICROBIAL SKIN FLORA

CROSS-REFERENCE TO RELATED APPLICATION

This application claims the benefits of U.S. Provisional Patent Application No. 62/130921 filed Mar. 10, 2015, the contents of which are hereby incorporated by reference herein.

FIELD OF THE INVENTION

This invention relates to skin treatments prior to a medical procedure and uses of silicone gel dressings having particulates of an antimicrobial dispersed in the gel sheet.

BACKGROUND

Skin is a natural barrier against microbes. Surgery and other invasive medical procedures involve opening of a subject's skin and thus provide an opportunity for infectious microbes to enter and cause infection via a contaminated insertion or incision site.

Skin infections incurred as a response to treatment such as surgery, injection or catheter or intravenous line insertion are a substantial health care concern. For example, in the United States, approximately 46 million surgeries are performed annually and at least 1% of surgeries involve complication by a surgical site infection, resulting in some cases in increased length of hospital stay, increased morbidity and even increased rates of mortality.

Skin infections caused by antibiotic-resistant bacteria such as methicillin-resistant *Staphylococcus aureus* (MRSA), Gram-negative rods, and *Candida* species are of particular concern within a hospital setting, as such infections may be spread between patients and are difficult to control once such an infection takes hold.

For surgical wounds, contamination may occur during surgery or post-surgery while the surgical wound heals, particularly if the site of the surgical incision or insertion is not properly prepared before surgery or maintained after surgery. In order to reduce risk of contamination and infection, a surgical site can be disinfected prior to surgery in order to reduce microbial load on the skin at the time of surgery.

SUMMARY OF THE INVENTION

The invention relates to use of one or more silicone-based dressings to be applied to a skin site on a subject prior to a medical procedure that involves breaching the skin, in order to reduce risk of infection of a wound that will be incurred during the medical procedure. Skin possesses native microbial flora, and the application of the dressing may reduce microbial load on the skin at a site at which an invasive medical procedure, such as an incision or insertion that punctures the skin, is to be performed, and may even sterilize the site prior to the procedure.

The dressings comprise a silicone gel sheet, which may include particulates of an antimicrobial dispersed in the gel sheet. The silicone gel sheet is self-adhesive and may be transparent. As well, the gel sheet is soft, flexible and porous. In some embodiments, the dressing may also have a non-adhesive and breathable backing layer coated on the silicone gel sheet.

The above features, as well as other features of the dressings allow for methods of reducing microbial load at an incision, insertion, injection or puncture site on a subject's skin by leaving the dressing in place for a period of time to allow for diffusion of the antimicrobial from the gel sheet to the skin of the subject covered by the dressing.

Thus, the use of the antimicrobial dressings comprising the silicone gel sheet may allow for a single application prior to a medical procedure in order to reduce microbial load at the site of the procedure. Because only a single application of the dressing is needed, the application may be done at home, either by the subject or under supervision by medical personnel, or in a medical setting by medical personnel. The ease of application and need for only a single application, which can be done during a pre-operative consultation, may allow for increased patient compliance as compared with typical at-home cleaning regimens involving antimicrobial gels, washes, soaps and/or wipes.

The length of time the dressing is applied to the subject's skin site and ongoing antimicrobial action prior to and up until the procedure, which time period may be as long as 7 days prior to the procedure, may also help reduce the microbial load and thus reduce the risk of infection of the wound site. The dressings used may provide sustained release of low concentrations of antimicrobial over the application period, which may help reduce skin irritation and which may inhibit microbial colonization and regrowth during the application period.

The silicone gel sheet dressings used in the method contain particulates of an antimicrobial, which design may allow for high loading of antimicrobial agents while providing sustained release of the antimicrobial once the dressing is in place on the skin site on the subject.

The flexible and self-adhesive nature of the silicone-based dressing allows for the dressing to be designed to fit specific regions on a subject where surgery or other invasive medical procedures that breach the skin may be performed, which may traditionally be awkward to dress because of the shape or movement of the part of the body where the medical procedure is to be performed. For example, the dressing can be designed to specifically wrap around a subject's knee in the case of knee surgery, which is a common surgical site that may be difficult to dress.

Thus, in one aspect, the invention provides a method for reducing microbial load at a site on the skin of a subject, the method comprising: applying a dressing over the site on the skin of the subject at which a medical procedure is to be performed, the dressing comprising a self-adhesive silicone gel sheet comprising at least about 95 wt % silicone and up to about 5 wt % of particulates of an antimicrobial dispersed in the silicone; and leaving the dressing in place to allow the antimicrobial to diffuse onto the site; wherein the dressing is applied with the silicone gel sheet contacting the skin of the subject and wherein the medical procedure involves breaching the skin.

Reducing microbial load at the site on the skin of the subject may comprise reducing, minimizing or preventing colonization or migration of microbes at the site, and/or reducing microbial load at the site on the skin of the subject comprises reducing, minimizing or preventing microbial colonization of the dressing.

The dressing may further comprise a backing layer coated on one side of the silicone gel sheet. The backing layer may comprise polymer, fabric or paper. In some embodiments, the backing layer comprises a polymer selected from the group consisting of polyester, polyethylene, polyvinyl chloride and polyurethane.

The silicone gel sheet of the dressing may comprise from about 95 wt % to about 99.9 wt % silicone. As well, the silicone gel sheet of the dressing may comprise about 0.1 wt % to about 5 wt % of the antimicrobial.

The antimicrobial may comprise an insoluble form of chlorhexidine, silver, polyhexamethylene biguanide, octenidine, or halamine, or any combination thereof. In some embodiments, the antimicrobial comprises an insoluble form of chlorhexidine. In some embodiments, the antimicrobial comprises photo-stabilised silver.

In some embodiments, the dressing comprises a combination of two or more antimicrobials. In some embodiments, the antimicrobial comprises a combination of an insoluble form of chlorhexidine and a photo-stabilised silver salt.

The insoluble form of chlorhexidine may be chlorhexidine free base, chlorhexidine diacetate, chlorhexidine dihydrochloride, or any combination thereof.

The photo-stabilised silver may be silver sulfate, silver phosphate, silver citrate, silver nitrate, silver acetate, silver lactate or any combination thereof.

The dressing is left in place for up to 7 days, and may be left in place up until the medical procedure is to be performed.

The medical procedure may comprise breaching the skin by injection, incision or insertion through the skin.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
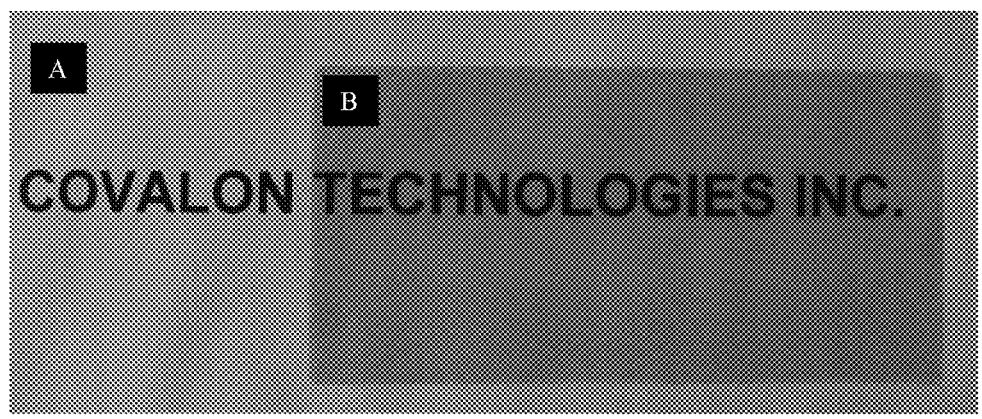
FIG. 1 is an image showing the transparency of a dressing exemplary of an embodiment of the invention: region (A) shows a portion ("COVALON") of a print-out free from the dressing and region (B) shows another portion ("TECHNOLOGIES INC.") of the print-out having the transparent gel sheet dressing placed over top.

There is provided a method of treating a site on the skin of a subject in order to reduce microbial load at the site. The treatment occurs prior to a medical procedure performed on a subject that breaches or compromises the integrity of intact skin, in order to reduce microbial load at the skin site prior to breaking the skin during the procedure, for example, a medical procedure that involves incision, injection or insertion through the skin. The method uses a dressing comprising a silicone gel sheet having dispersed particulates of an antimicrobial, thus protecting the skin while allowing for moisture evaporation and oxygen exchange to maintain skin health prior to and/or following the medical procedure.

As used herein, reference to reduction of microbial load or reducing microbial load on the skin site on the subject includes reduction, minimization or elimination of the number of microbes at the site on the skin at which the microbial load is to be reduced. Reduction of or reducing microbial load may include reducing, minimizing or preventing microbe migration onto the skin site, by reducing, minimizing or preventing further microbial colonization at the skin site under the physical barrier of the dressing, and may also reduce, minimize or prevent further microbial colonization at skin adjacent to the dressing due to diffusion and absorption of the antimicrobial into the skin. Reduction of or reducing microbial load may also include sterilization of the skin site, which results in a microbial count of substantially zero, or zero, at the skin site. The reduction of or reducing microbial load may occur at the skin covered by the dressing and also skin adjacent to the dressing due to diffusion and absorption of the antimicrobial agent over time. As well, reduction of microbial load may be facilitated by the effect of the particulates of antimicrobial within the dressing, which reduce, minimize or prevent microbial colonization of the dressing itself.

In the method, the silicone gel sheet dressing comprising an antimicrobial agent is applied prior to the medical procedure, on the site on the subject's skin.

The skin at and around the skin site at which the dressing is to be applied may be first briefly cleaned using a cleanser, for example mild soap or alcohol solution, for example by wiping or swabbing the desired area. This pre-treatment may allow for removal of any cosmetics, lotions, oils, dirt, etc. that may be on the skin surface. While optional, the cleaning step can provide a skin surface to which the silicone gel sheet dressing may better adhere.

In the method, the site at which the dressing is applied encompasses the location on the skin surface of the subject in the vicinity of where a skin breach, such as an incision, insertion or injection is to be made or has been made during a medical procedure. For example, a site at which a surgical incision is to be made, or at which a catheter or intravenous line is to be inserted. Ideally, the skin site will have clean, substantially unbroken skin that is generally free from irritation prior to application of the silicone-based dressing, although depending on the health of the subject's skin, the method may be performed on irritated skin or skin having blemishes or minor sores. Thus, as used herein, reference to the skin site, or to the site on the skin of a subject, is to the region of skin that is to be covered or is covered by the dressing, and which includes the site at which the medical procedure is to be performed. The effect of the dressing may also influence surrounding skin adjacent to the skin site, due to diffusion or absorption of the antimicrobial into the skin.

The dressing is applied to the optionally cleaned skin of the subject, so as to cover the skin site, including the location at which the skin breach is to occur and surrounding skin.

The dressing comprises a silicone gel sheet having dispersed particulates of an antimicrobial, and optionally having a backing layer coated on the gel sheet.

The silicone gel sheet is a cured gel sheet, meaning that the sheet is a layer formed by curing a silicone gel mixture that contains any components required to be in the final gel sheet, such as particulates of an antimicrobial.

The silicone gel sheet may comprise a crosslinked silicone elastomer. Silicone elastomers are in the form of liquids, gels or rubber and can be molded and cured to form gel sheets, which may be tacky to the touch and thus may have adhesive properties. Any type of silicone elastomer may be used, including for example Dow Corning's soft skin adhesive silicone gel, SILGEL™ by Wacker Chemie GmbH, Germany, and MED-6345™ by Nusil Technology.

The silicone gel sheet comprises at least about 95 wt % silicone, or at least about 96 wt % silicone, or at least about 97 wt % silicone, or at least about 98 wt % silicone. In some embodiments, the silicone gel sheet comprises from about 95 wt % to about 98 wt % silicone, or from about 96 wt % to about 97 wt %, or about 97 wt %.

As the gel sheet is a cured gel sheet formed from a silicone elastomer, the gel sheet does not require any substrate for support or cohesion, and is in the form of a stand-alone sheet, which may be formed by molding a pourable mixture containing a silicone elastomer and subsequently curing the molded mixture to form a gel sheet. The cured gel sheet is tacky and self-adhesive, and forms a soft, flexible and cohesive layer. It should be noted that although the gel sheet is capable of being used as a stand-alone sheet, the gel sheet may have an optional backing layer applied.

As indicated above, the gel sheet has tackiness, meaning the gel sheet is sticky to the touch and yet maintains cohesiveness. The silicone gel sheets as used in the method have sufficient tackiness to allow the dressing to adhere to a subject's skin. Thus, the silicone gel sheet is self-adhesive, meaning that due to the properties of the cured and crosslinked silicone elastomer, no adhesive component such as a glue or paste is required in the dressing to keep the dressing in place over a skin site on a subject, even when worn throughout the subject's daily routine.

Adhesiveness may be measured using standard adhesions tests, for example, measuring the force required to peel the gel sheet from a surface. For example, in some embodiments, the gel sheet may have an adhesiveness of about 1.3 to about 2.5 N/25 mm.

The thickness and weight of the silicone gel sheet may vary according to the particular location of the skin site on the subject on which the dressing is to be used, and may also depend on the moisture vapor transmission rate required for a particular location of a skin site. Typically, the thickness may vary from tens of microns up to several millimeters (mm) such as 0.05 mm to 3.0 mm. For example, if the dressing is applied to a vascular access puncture site, a thin dressing may be utilized. Such a thin layer may be from about 50 to 200 microns, in aspects from about 100 to 150 microns.

The loosely crosslinked nature of the silicone gel sheet allows the silicone polymers to remain flexible and facilitates the diffusion of gas molecules, such as oxygen and water vapour, through the silicone gel sheet, thus making the gel sheet breathable.

Further, the silicone gel sheet is cohesively strong, and thus can be formed and used in the dressing without the need of any supporting substrate, provided that the gel sheet is sufficiently thick, for example about 1 mm in thickness or greater. Cohesively strong means that the silicone gel sheet may be applied to a surface and subsequently removed with no or minimal residue left on the surface, possibly due to sufficiently strong intermolecular bonding (i.e. crosslinking) between silicone polymer chains in the gel sheet, even with included particulates of antimicrobial.

Cohesiveness may be measured using standard cohesion tests, for example, using simulated peeling test in which any residue remaining on a test surface after peeling is weighed. In some embodiments, the gel sheet may have a cohesiveness that results in residue of about 0.32 mg/cm$^2$ of dressing, or less.

The silicone gel sheet in the dressing is soft. The softness or consistency of cured silicone can be measured using standard techniques, for example with a penetrometer involving the ability of a hollow cone of fixed weight to penetrate the silicone gel during a fixed time. A typical international standard used is ISO 2137. In some embodiments, the silicone gel sheet may have a penetration after cure value of from about 25 to about 200 mm/10, or for example about 140 mm/10.

In the dressing, the silicone gel sheet also comprises particulates of an antimicrobial. Reference to particulates of the antimicrobial means that the antimicrobial is undissolved in the silicone, and is dispersed throughout the silicone gel sheet as fine solid particles, such as a powder or granules. The particulates may be visually observable through any suitable microscopic instrument such as an optical microscope or scanning electron microscope, or possibly with the naked eye. If desired, the gel sheet may comprise particulates of more than one antimicrobial agents.

The antimicrobial is included in particulate form in order to maintain cohesion of the silicone gel sheet while allowing for high concentration of antimicrobial in localized areas surrounding a particulate. The strength and adhesive properties of a silicone gel sheet may be compromised if significantly diluted by addition of a large amount of an incompatible liquid component. The inclusion of particulates in the dressings described herein thus minimizes impact on cohesive strength and adhesiveness of the silicone gel sheet.

As well, the use of particulates allows for slow diffusion of the antimicrobial from the gel sheet toward the subject's skin, resulting in sustained release of the antimicrobial while the dressing is in place over the skin site on the subject.

The particulates of the antimicrobial may be, in some embodiments, from about 0.01 to about 100 microns, or from about 10 to about 50 microns, in diameter.

As indicated above, the gel sheet may comprise one or more antimicrobial. Each antimicrobial included in the gel sheet may be in particulate form.

The particulates of the antimicrobial are substantially evenly distributed throughout the silicone gel sheet, both in terms of even distribution across the area of the silicone gel sheet that is in contact with the subject's skin, and in terms of even distribution throughout the depth of the silicone gel sheet. Such distribution contributes to the slow migration of the antimicrobial from the silicone gel sheet onto the skin site.

The concentration of the antimicrobial in the silicone gel sheet may be up to about 5 wt % total antimicrobial in the cured gel sheet, as greater amounts of particulates may interfere with the properties of the gel sheet and thus affect the performance of the dressing. The amount of each antimicrobial included in the gel sheet may vary depending on the potency of a particular antimicrobial or the combined potency if more than one antimicrobial is included in the gel sheet. Thus if more than one antimicrobial is included in the gel sheet, the combined total wt % may be up to about 5 wt %. The concentration of the antimicrobial thus may be from about 0.1 wt % to about 5 wt %, from about 1 wt % to about 5 wt % from about 2 wt % to about 5 wt %, from about 2 wt % to about 3 wt %, or about 3 wt %. The concentration of the antimicrobial may be any given value falling in the range of from about 0.1 wt % to about 5 wt %.

The antimicrobial may be, in some embodiments, an insoluble form of chlorhexidine, silver, polyhexamethylene biguanide, octenidine, or halamine, or any combination thereof.

In some embodiments, the antimicrobial is an insoluble form of chlorhexidine. Chlorhexidine [1,1'-hexamethylene-bis[5-(4-chlorophenyl)-biguanide] is a strong base and practically insoluble in water (0.008% wt/vol at 20° C.). It reacts with acids to form salts with variable solubility in water and is most stable in the form of salts, such as the digluconate, diacetate, and dihydrochloride. Chlorhexidine and its salts are known for their antimicrobial activity against a wide range of Gram-positive and Gram-negative organisms, yeast, fungi, facultative anaerobes, and aerobes [Denadai et al. Superamolecular self-assembly of b-cyclodextrin: an effective carrier of the antimicrobial agent chlorhexidine, Carbohydrate Research 2007; 342: 2286-2296]. A suitable insoluble chlorhexidine compound is typically chlorhexidine or a chlorhexidine salt that exists substantially as a solid at ambient temperature. Suitable insoluble forms of chlorhexidine include chlorhexidine free base, chlorhexidine diacetate, chlorhexidine dihydrochloride, or any combination thereof.

In some embodiments, the antimicrobial is an insoluble form of silver, including insoluble silver salts. Antimicrobial silver agents are known to have general antimicrobial properties directed against a wide range of bacteria and fungi. The antimicrobial silver may be provided as a silver salt. Examples of suitable silver salts include, for example, silver sulfate, silver phosphate, silver citrate, silver nitrate, silver acetate, silver lactate and any combination thereof.

The silver may be photo-stabilised to deter photo-induced discoloration. Photo-stabilisation of silver compounds is described, for example, in U.S. Patent Publication No. 2009/0035388 to Dudnik et al.

The silver antimicrobial may be photo-stabilised with (i) a compound containing a basic nitrogen atom to complex with silver as is understood by a skilled person in the art and (ii) a dye. Complexing silver with the compound containing a basic nitrogen atom may prevent the silver from subsequent oxidation/reduction reactions that would lead to discoloration of the silver and thus discolouration of the dressing. The dye may also protect the silver from subsequent reduction reactions that would cause color changes in the silver.

Suitable compounds containing a basic nitrogen atom includes one or more of ammonia, tris(hydroxymethyl)aminomethane, pyrrolidone carboxylic acid (D,L-pyroglutamic acid), polyethyleneimine, and amino acids. Suitable amino acids include alanine, arginine, asparagine, cysteine, glutamine, glutamate, glycine, histidine, isoleucine, lysine, methionine, phenylalanine, proline, serine, threonine, tryptophan, tyrosine and valine and any combination thereof.

Suitable dyes include any cationic triarylmethane dye such as, for example, Brilliant Green, Malachite Green, Methylene Blue, Ethyl Violet, Crystal Violet, Victoria Blue R, Victoria Blue B and Victoria Pure Blue BO and any combination thereof. Suitable dyes may be commercially available from Sigma-Aldrich, U.S.A.

In some embodiments, D,L-pyroglutamic acid and Brilliant Green may be used to photo-stabilise a silver agent such as silver acetate.

The photo-stabilisers, such as the compound containing a basic nitrogen atom and the dye will be complexed or reacted with the silver, and thus will be included as part of the particulates, if photo-stabilised silver is included as an antimicrobial. Thus, for the concentrations recited herein, when photo-stablised silver is used as an antimicrobial, the concentrations refer to the photo-stablised form and not only the silver agent alone.

The dressing may optionally comprise a backing layer coated on one side of the silicone gel sheet. When included in the dressing, the backing layer is coated on the side of the dressing that faces away from the subject's skin when the dressing is in place over the skin site.

When included in the dressing, the backing layer is non-adhesive. The backing layer may comprise a non-adhesive polymer film, fabric or paper layer, or other suitable breathable, non-adhesive material. Breathable polymer films are frequently used as backing layers for wound dressings and suitable polymer films are known in the art, for example polyester, polyethylene, polyvinyl chloride or polyurethane.

The backing layer is breathable, in order to allow excess moisture to evaporate from the skin surface and to allow for oxygen to reach the skin. As well, any volatile organic compounds emitted from the subject's skin may pass through the dressing including through the backing layer. The backing layer may have a moisture vapor transmission rate of at least 500 g/m$^2$/d, at least 1000 g/m$^2$/d, or at least 1500 g/m$^2$/d.

In some embodiments, the backing layer has a thickness of from about 0.025 to about 0.25 mm (or about 1 mil to about 10 mils).

The backing layer is non-adhesive, thus preventing the exposed side of the dressing from attracting dirt and dust and from sticking to the subject's clothes while the dressing is worn.

As well, the backing layer may also prevent diffusion of the antimicrobial from the outer surface of the dressing, or from being washed out, for example during showering or bathing while the subject is wearing the dressing. The backing layer may contribute to the protective effect of the dressing, helping to protect the skin around the skin site from dirt and from further microbial colonization during the application period.

Thus, the silicone gel sheet comprising the particulates of the antimicrobial may optionally have the backing layer coated on one side of the gel sheet. The silicone gel sheet makes contact with the subject's skin when in place over the skin site, via a side of the gel sheet that does not have a coated backing layer, thus facing the side of the dressing that may have a backing layer away from the subject's skin.

The dressing is applied to the area of the subject's skin so that it covers the site at which the medical procedure is to be performed and surrounding skin, with the silicone gel sheet contacting the subject's skin. In this way, the antimicrobial contained in the gel sheet diffuses out of the gel sheet and onto the skin surface under and around the dressing and, in some cases, may be slowly absorbed into the skin, while the dressing is worn during the application period.

Additionally, the inclusion of the particulates of the antimicrobial, and the effect of the slow diffusion of the antimicrobial throughout the dressing, help to prevent the dressing itself from becoming contaminated with any microbes during the time period that the dressing is in place on the subject's skin, even when the dressing is exposed to moisture during the course of the subject's daily routine.

The optional cleaning of the skin and the application of the dressing is straightforward and may be performed by anyone, including the subject. However, in order to increase patient compliance, the method may be performed in a medical setting, for example a doctor's office or in a hospital during a pre-operative consultation with the subject. Thus, the subject may perform the method, either at home independently or as guided by medical personnel, or in a medical setting under the supervision of medical personnel, including for example a doctor, a nurse, a nursing assistant or other medical personnel. Alternatively, the medical personnel may perform the method, which may increase comfort of the subject if done during a pre-operative consultation meeting, as well as better ensuring patient compliance.

Once applied, the dressing may be left in place for the duration of the application period is defined as the time from application of the dressing until removal for preparation of the subject for the medical procedure. The application period may be up to 7 days, up to 6 days, up to 5 days, up to 4 days, up to 3 days, up to 2 days, up to 1 day. For example, the application period may be from about 2 to about 7 days, or may be from about 3 to about 5 days.

Thus the subject may wear the dressing over the skin site during the course of their daily routine throughout the application period leading up to the scheduled medical procedure, and may be kept in place while showering or bathing. Although the nature of the silicone gel sheet layer allows for a single dressing to be applied and to remain in place for the duration of the application period and to withstand the strain of typical daily wear, the dressing may be changed during the application period if necessary, for example if the dressing has become accidentally damaged or dislodged.

During the application period, the dressing is used to disinfect the site at which the medical procedure is to be performed and surrounding skin. Disinfect, disinfection and disinfecting as used herein refer to reduction of microbial load on the skin that is in contact with the silicone gel sheet containing the particulates of antimicrobial. The antimicrobial may act to kill some, the majority of, most, or even all microbes present on the relevant region of skin at the time of application, although it will be appreciated that a few microbes may remain, as it may be difficult to completely sterilize the skin surface. The antimicrobial may act to inhibit or slow growth or regrowth of existing microbes. Thus, the reduction of microbial load on the skin surface in contact with the silicone gel sheet of the dressing may help to reduce risk of infection of the wound occurring during or after the medical procedure, as fewer microbes may be introduced into the wound via contamination from the skin surface.

The dressing comprising the antimicrobial may target any type of microbe typically found on skin, including for example, viruses, bacteria, funguses, or parasites that may be present on the skin site at the time of application of the dressing.

Due to the nature of the silicone that forms the gel sheet and due to the particulate form of the included antimicrobial, the antimicrobial is gradually released from the gel sheet and onto or into the skin of the subject that is in contact with the silicone gel sheet layer during the application period. Silicone gel is typically loosely crosslinked and flexible and thus allows for the particulates of the antimicrobial to migrate over time. The slow, sustained release of antimicrobial helps provide antimicrobial activity to the skin surface throughout the application period, and thus may provide a prolonged period of antimicrobial treatment prior to the medical procedure.

The use of particulates of the antimicrobial also allows for relatively high amounts of antimicrobial to be included in the dressing while reducing risk of skin irritation that can arise from a high dose of certain antimicrobials.

As well, the dressing serves as a physical barrier on the skin over the entire application period, thus preventing introduction of new microbes to the region of skin covered by the dressing. This physical protection in combination with sustained antimicrobial release over the length of the application period contributes to reducing microbial load on the region of skin covered by the dressing.

The dressing is then removed at the end of the application period. This may be done at the time of prepping the subject for the medical procedure, and thus immediately or shortly prior to the breach of the skin. Thus, the removal may occur under controlled conditions designed to minimise introduction of new microbes to the skin site once the dressing is removed. For example, the dressing may be removed by medical personnel at the time the skin is ready to be cleaned prior to commencement of surgery.

Thus, the method as described above uses a dressing having a silicone gel sheet that comprises at least about 95 wt % silicone and which is placed against the subject's skin. The use of such a dressing may provide certain features that contribute to the advantages of the method.

The silicone gel sheet is self-adhesive, meaning that the gel sheet may adhere onto a surface, including skin, without the use of any additional substance typically used as an adhesive, such as a glue or paste. Thus, the dressings adhere to the skin surface to which they are applied without the need for any adhesives, bandages or tapes.

Cohesive strength of the gel sheet, and thus of the dressings, may be maintained when other components added to the silicone total no more than about 5 wt % of the silicone gel sheet, i.e. when the silicone gel sheet comprises at least about 95 wt % silicone. If the gel sheet contains less than about 95 wt % silicone, the gel sheet may not be strong enough to main integrity upon removal from the skin of a subject and thus may leave silicone residue on the skin surface.

The dressings are soft and comfortable, and may readily be worn for an extended period without discomfort.

The dressings are also flexible and can therefore be contoured to the shape of the skin surface at the site of application. The dressing may be sized and shaped to fit the appropriate skin region for a particular subject that is to undergo a medical procedure.

Figure 2:
FIG. 2 is a schematic drawing of a dressing exemplary of an embodiment of the invention.

As well, depending on the particular material used for the backing layer, for example polymer film, the dressings may be transparent, allowing the skin covered by the dressing to be viewed throughout the application period, which may allow for monitoring for any irritation that may develop during the application period. The transparency also helps render the dressing relatively unobtrusive while worn by the subject during the course of daily activities. FIG. 1 depicts a transparent dressing as described herein, the dressing comprising a self-adhesive gel sheet without any backing layer. FIG. 2 is a schematic drawing of the gel sheet.

Since the dressing may be applied days before the medical procedure, in the case of surgery the dressing may also help prevent wrong side surgery. That is, the subject will wear the dressing for a period of up to 7 days prior to surgery, and thus may alert the medical team if the wrong side of the subject is being treated. In addition, due to the time period between application and removal at the time of preparation for surgery, additional confirmations by the surgical team can be made, thus reducing the risk that surgery is performed on the wrong side of the subject.

The dressings, including the silicone gel sheet and the optional coated backing layer may be moisture vapor permeable with a moisture vapor transmission rate greater than that of normal healthy skin, i.e. 204±12 $g/m^2/d$. Thus, the dressings may not cause maceration of healthy skin to which they may be applied for the duration of the application period.

The thickness and weight of the dressing may vary according to the particular region of the body on which it is to be used, as well as the type of surgical wound involved and the moisture vapor transmission rate required for healing of that wound type. Typically, the thickness may vary from tens of microns up to several millimeters (mm).

For dressings containing an antimicrobial, due to the nature of the silicone gel sheet and due to the particulate form of the included antimicrobial, the antimicrobial may be gradually released from the gel sheet and onto or into the skin of the subject that is in contact with the silicone gel sheet during the relevant application period. Silicone gel that is loosely crosslinked is typically sufficiently flexible to allow migration of the particulates of the antimicrobial over time. The slow, sustained release of antimicrobial helps provide antimicrobial activity to the skin surface throughout the relevant application period, allowing for relatively high amounts of antimicrobial to be included in the dressing while reducing risk of skin irritation that can arise from a high dose of certain antimicrobials.

The method may be suitable for use even on subjects with sensitive skin or that react to high concentrations of certain antimicrobials. Silicone tends to be minimally irritating to skin, possibly in part due to its inertness and cohesive strength, and thus the use of the silicone gel sheet in direct contact with the skin can reduce irritation at the skin site, even with long application periods of up to 7 days. The slow, sustained release of any antimicrobial from the particulates included in the silicone gel sheet for the duration of the period that the dressing is applied may also contribute to the minimal or non-irritating nature of the dressings.

In the method, the dressing may be sized and shaped as required for the particular region of the body where the skin site is located.

By sizing and shaping the dressing to fit specific regions of a body, the method may be used for wide variety of different skin sites. For example, the dressings may be contoured to fit curved or flexible regions of skin, such as the skin surrounding a surgical site on a knee of a subject.

For use in the method, the dressing may be packaged with a release liner on any side of the silicone gel sheet that does not have a coated backing layer. The release liner may be made of a non-adhesive material, such as polycarbonate, polyethylene, or wax paper, may be used to cover and protect any uncoated surface of the silicone gel sheet prior to applying the dressing.

The dressing may be provided in sterilized form, and may be kept in a sterile package such as a paper/paper, paper/plastic, Tyvek®/plastic, or Tyvek®/Tyvek® pouches. Sterilization may be achieved in a conventional manner, e.g. heat or ethylene oxide. During use, the sterile dressing is removed from the pouch, any release liner is removed from the surface of the silicone gel sheet and the dressing is applied to the skin site.

Also contemplated herein are various uses of the dressing as described herein, for treating a treating a site on the skin of a subject in order to reduce microbial load at the site, to reduce risk of infection during a medical procedure that involves breach of a subject's skin. The use may occur prior to the medical procedure for a period of up to 7 days.

The described embodiments are susceptible to many modifications of form, arrangement of parts, details and order of operation. The invention, rather, is intended to encompass all such modifications within its scope, as defined by the claims.

The methods and devices described herein are further exemplified by the following non-limiting examples, which are described for the purposes of illustration and are not intended to limit the scope of the invention.

EXAMPLES

Example 1

Antimicrobial Activity Test—Time-Kill Test

A GLP-compliant and modified ISO 22196 assay was performed to monitor the antimicrobial activity of silicone dressings over time.

The log reductions of microorganisms inoculated onto antimicrobial silicone dressings were determined by harvesting the samples after 0, 12, 24, 96, and 168 hours of incubation, enumerating viable organisms and subtracting the average of the common log of the number of viable organisms recovered at a defined contact time from that immediately after inoculation.

Eight microorganisms were used in this test, which included *Candida albicans, Candida tropicalis, Enterobacter cloacae, Klebsiella pneumoniae, Pseudomonas aeruginosa, Staphylococcus aureus* (MRSA), *Staphylococcus epidermidis*, and *Enterococcus faecalis* (VRE).

Antimicrobial dressings aged for 13 months at 25$^\circ$ C.±2° C./60% RH±5% RH were used in this study. All tests were performed in triplicate.

The test results demonstrated that antimicrobial silicone dressings can provide effective antimicrobial activity (i.e. 4-log reduction with a $1\times10^6$ inoculum) against gram-positive and gram negative bacteria as well as yeast over 7 days as shown in Table 1.

TABLE 1

Average log reduction of microorganisms by antimicrobial silicone dressings.

| Time (h) | C. albicans | C. tropicalis | E. cloacae | K. pneumoniae | P. aeruginosa | S. aureus (MRSA) | S. epidermidis | E. faecalis (VRE) |
|---|---|---|---|---|---|---|---|---|
| 12 | >5.34 | >5.70 | >6.15 | >6.02 | 5.55 | 4.21 | 4.77 | 4.95 |
| 24 | >5.34 | >5.70 | >6.15 | >6.02 | >5.89 | >5.33 | >4.87 | >6.08 |
| 96 | >5.34 | >5.70 | >6.15 | >6.02 | >5.89 | >5.33 | >4.87 | >6.08 |
| 168 | >5.34 | >5.70 | >6.15 | >6.02 | >5.89 | >5.33 | >4.87 | >6.08 |

Example 2

Human Regrowth Prevention Study

The capacity of antimicrobial silicone dressings to suppress floral regrowth following cutaneous prepping for one minute with 70% isopropyl alcohol was evaluated in this study, which was a within-subjects randomized design where each subject served as his or her own control by using five test sites per test area.

A total of 37 volunteers were enrolled and 34 completed the study.

On study day 0, two skin sites located in the center of the two test areas were sampled for baseline floral counts. Using a randomization schedule, one test area (right or left) was prepped with 70% isopropyl alcohol for one minute. After the site air dried, an immediate post-prep floral sample was obtained and the test dressings were applied following a randomization schedule. The dressings were left in place for 4 or 7 days.

Quantitative skin cultures by the Williamson-Kligman scrub cup technique were obtained from one side (by random assignment) after 4 days and the contralateral side after 7 days. Two locations on the skin underneath each dressing were sampled using the scrub cup technique. The areas sampled for the antimicrobial silicone dressings were under the center of each dressing and an area at least 1.0 cm distance from where the center sample was taken.

Regrowth measurement under the center of the dressings showed that the microbial population under the antimicrobial silicone dressing was not significantly different from the alcohol post-prep population after 4 and 7 days of dressing wear ($p > 0.05$).

With regard to the regrowth measurement from the off-center site, the microbial population of the antimicrobial silicone dressing after 4 and 7 days was not significantly different from the alcohol post-prep population ($p < 0.05$).

The antimicrobial silicone dressings containing chlorhexidine and silver were effective in suppressing microbial re-growth on intact skin under the entire surface of the dressing for up to 7 days, suggesting that the risk of infection associated with subsequent procedures that compromise skin integrity may be substantially reduced.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

All lists and/or ranges provided herein are intended to include any sub-list and/or narrower range falling within the recited list and/or range, including individual items on a list or individual values falling within a range.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for reducing microbial load at a site on the skin of a subject in preparation for a subsequent medical procedure that involves breaching the skin of the subject, the method comprising:

up to 7 days prior to when the subsequent medical procedure is to be performed, applying or having the subject apply a dressing over the site on the skin of the subject at which the medical procedure is to be performed, at which site the skin of the subject has not yet been breached by the medical procedure, the dressing comprising a self-adhesive silicone gel sheet comprising at least about 95 wt % silicone and up to about 5 wt % of particulates of an antimicrobial dispersed in the silicone, the dressing applied with the silicone gel sheet contacting the skin of the subject;

leaving the dressing in place up until the time when the subject is to be prepared for the subsequent medical procedure, to allow the antimicrobial to diffuse onto the site, thereby reducing the microbial load on the skin contacted by the silicone gel sheet to sterilize the site on the skin in preparation for the subsequent medical procedure; and removing the dressing.

2. The method of claim 1, wherein the dressing further comprises a backing layer coated on one side of the silicone gel sheet.

3. The method of claim 2, wherein the backing layer of the dressing comprises a polymer, fabric or paper.

4. The method of claim 2, wherein the backing layer of the dressing comprises a polymer selected from the group consisting of polyester, polyethylene, polyvinyl chloride and polyurethane.

5. The method of claim 1, wherein the silicone gel sheet of the dressing comprises from about 95 wt % to about 99.9 wt % silicone.

6. The method of claim 1, wherein the silicone gel sheet of the dressing comprises about 0.1 wt % to about 5 wt % of the antimicrobial.

7. The method of claim 1, wherein the dressing comprises a combination of two or more antimicrobials.

8. The method of claim 1, wherein the antimicrobial comprises an insoluble form of chlorhexidine, silver, polyhexamethylene biguanide, octenidine, or halamine, or any combination thereof.

9. The method of claim 8, wherein the antimicrobial comprises an insoluble form of chlorhexidine.

10. The method of claim 8, wherein the antimicrobial comprises a combination of an insoluble form of chlorhexidine and a photo-stabilised silver salt.

11. The method of claim 9, wherein the insoluble form of chlorhexidine is chlorhexidine free base, chlorhexidine diacetate, chlorhexidine dihydrochloride, or any combination thereof.

12. The method of claim 8, wherein the antimicrobial comprises photo-stabilised silver.

13. The method of claim 12, wherein the photo-stabilised silver is silver sulfate, silver phosphate, silver citrate, silver nitrate, silver acetate, silver lactate or any combination thereof.

14. The method of claim 1, wherein the dressing is left in place for up to 7 days.

15. The method of claim 1, wherein the subsequent medical procedure is to comprise breaching the skin by injection, incision or insertion through the skin.

16. The method of claim 1, wherein the dressing that is applied is a first dressing, the method further comprising, prior to said leaving the dressing in place, replacing the first dressing with a replacement dressing having the same composition as the first dressing.

17. The method of claim 1, wherein the applying or having the subject apply the dressing is done during a pre-operative consultation with the subject.

* * * * *